United States Patent

Peng et al.

Patent Number: 5,158,532
Date of Patent: Oct. 27, 1992

[54] ARTICULATED SWAB

[76] Inventors: Mike Peng, 6200 Edinger - #409, Huntington Beach, Calif. 92647; Nishizaki Kazuhiro, 4302 Pickwick Cir. #201, Huntington Beach, Calif. 92649

[21] Appl. No.: 753,972
[22] Filed: Sep. 3, 1991
[51] Int. Cl.$^5$ ............... A61M 35/00; A47K 7/02; A46B 5/02
[52] U.S. Cl. ........................... 604/1; 604/2; 15/244.1; 15/229.11; 15/210.1; 15/144.1
[58] Field of Search ................... 604/1–3; 128/749, 759; 15/244.1, 244.2, 144 R

[56] References Cited

U.S. PATENT DOCUMENTS

| | | | |
|---|---|---|---|
| 3,346,187 | 10/1967 | Mueller | 239/33 |
| 3,409,224 | 11/1968 | Harp et al. | 239/33 |
| 3,438,578 | 4/1969 | Peterson et al. | 239/33 |
| 4,718,889 | 1/1988 | Blasius, Jr. et al. | 604/1 |
| 4,776,835 | 10/1988 | Lee | 604/1 |
| 4,795,421 | 1/1989 | Blasius, Jr. et al. | 604/1 |
| 4,820,259 | 4/1989 | Stevens | 604/2 |
| 4,935,001 | 6/1990 | George | 604/1 |
| 5,001,803 | 4/1991 | Discko, Jr. | 604/1 |

Primary Examiner—David Isabella
Assistant Examiner—A. Zuttarelli
Attorney, Agent, or Firm—Walter A. Hackler

[57] ABSTRACT

An applicator swab that includes an elongate support member with a swab head mounted on at least one end thereof, together with accordion-like folds disposed in the support member for adjustably disposing the swab head at an angle to a center portion of the elongate member. In addition, the accordion-like folds provide means for limiting the amount of pressure that can be exerted by the swab against an object by forcing of the swab against the object, and accordion-like folds in the support member beneath the swab head enable the swab head to adjust to different diameters which enhances the usefulness of the swab.

10 Claims, 1 Drawing Sheet

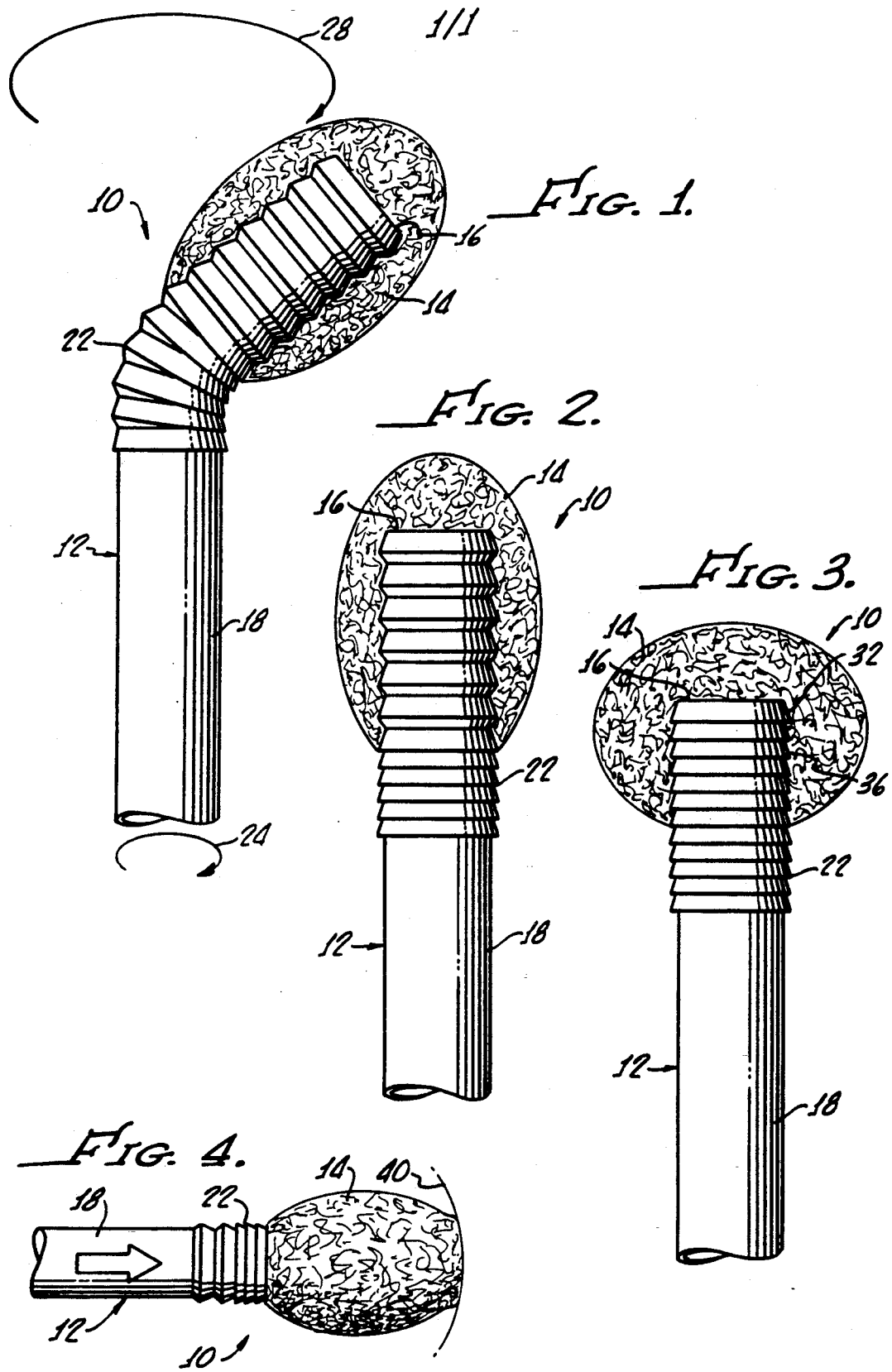

ARTICULATED SWAB

The present invention generally relates to applicator devices and more particularly is directed to an improved applicator swab having structure facilitating the cleaning of ears, the application of medication, and the application of cosmetic formulations.

Over the years, many types of applicator swabs have been made with the earliest of such swabs including a matted absorbent material such as cotton disposed on the end of a wood stick.

The coaxial alignment of the swab and the applicator stick is preferred in many uses. However, in certain applications, such as, for example, set forth in U.S. Pat. No. 4,776,835, swabs set in an obtuse angle to the applicator handle or stick are useful for application of medication accurately to portions of a person which would otherwise be difficult or impossible to reach.

More particularly, a conventional coaxial swab and applicator handle are not convenient to use for cleaning portions of the human ear. The funnel-shaped auricle of the ear, in many instances, provides a surface for cleaning which lends itself to an applicator with a swab disposed at an obtuse angle thereto.

Further, the varying size of the auricle makes it difficult to clean with a swab having fixed dimensions. Therefore, a set of swabs of varying swab tip size would be preferred for efficient cleaning of the human ear.

Since the ear, and most particularly, the eardrum and the auditory canal leading thereto are sensitive, injury thereto or discomfort to the user may occur with the use of ordinary swabs.

The articulated swab, in accordance with the present invention, overcomes many of the drawbacks of prior art swabs. In particular, the articulated swab, in accordance with the present invention, may be used in situations where a coaxial swab applicator handle is desired while at the same time, the swab may be disposed at an obtuse angle to the applicator stick for those situations in which this configu-ration is used to advantage.

Accordingly, in accordance with the present invention, a swab diameter may be changed and harmful use of the applicator may be inhibited by the structure of the present invention.

SUMMARY OF THE INVENTION

An applicator swab in accordance with the present invention generally includes elongate support member and a swab mounted on at least one end of the elongate support member with means for adjustably disposing the swab at an angle to a center portion of the elongate support member. Particularly, means may be provided for changing the diameter of the swab. This feature is important in adjusting the swab diameter to facilitate its use by persons having different sized auricles.

The elongate support member generally includes a tube and the means for adjustably disposing the swab comprises accordion-like folds in the tube between the swab and the center portion of the tube. In addition, the means for changing the diameter of the swab includes expandable accordion-like folds in the tube beneath the swab with the extension and collapsing of the folds causing a concomitant change in diameter of the swab.

Importantly, the accordion-like folds disposed beneath the swab and between the swab and the center portion of the tube are collapsible from the expanded state, thus limiting the amount of pressure that can be exerted by the swab through the forcing of the swab against an object with the elongate support member.

Various degrees of force and means for causing collapse of the accordion-like folds between the swab and the tube center portion before collapse of the accordion-like folds beneath the swab itself include adhesive means for bonding the swab to the accordion-like folds therebeneath.

BRIEF DESCRIPTION OF THE DRAWINGS

The advantages and features of the present invention will be better understood by the following description when considered in conjunction with the accompanying drawings in which:

FIG. 1 is a view of one end of an articulated swab in accordance with the present invention generally showing an elongate support member and a swab mounted on one end thereof with the swab being in partial cross-section in order to show accordion-like folds in the elongate support member beneath the swab, the swab being disposed at an obtuse angle to a center portion of the elongate member;

FIG. 2 is similar to the articulated swab shown in FIG. 1 with the swab and central portion of the elongate support member aligned in a coaxial manner;

FIG. 3 is another view of the articulated swab in accordance with the present invention in which the accordion-like folds are collapsed in order to change the diameter of the swab attached to the elongated member; and FIG. 4 illustrates the manner in which the articulated swab in accordance with the present invention may be utilized to limit the force or pressure that can be exerted by the swab against an object by forcing of the swab against the object with the elongate support member.

DETAILED DESCRIPTION OF THE DRAWINGS

Turning now to FIG. 1, there is shown an applicator swab 10 in accordance with the present invention generally including an elongate support member 12 having a swab 14 mounted on at least one end 16 of the elongate member.

It should be appreciated that while only one end of the applicator swab 10, in accordance with the present invention, is shown in the drawings, the other end (not shown) may be identical in structure or a center portion 18 of the elongate member 12 may terminate without a swab (not shown) disposed thereon.

Preferably, the elongate member 12 is of a tubular configuration made from any suitable plastic or the like. A plurality of accordion-like folds 22 disposed in the elongate member 12 provide a means for adjustably disposing the swab head 14 at an angle to the center portion 18 of the elongate support member. Any conventional fold configuration as may be well-known in the art for enabling a plastic tube, such as the elongate member 12, to be curved or bent without resiliently springing back to its original position may be suitable for use in the present invention. Folds 22 are only representative of such folds, and the techniques for manufacturing the tubular devices of this nature are well-known in the art.

Importantly, however, when the applicator swab 10 is in the "bent" configuration with the head 14 at an obtuse angle to the elongate member 18, the swab 10 when held by the central portion 18 facilitates application of medication or the application of cleaning solutions to articulate portions of an ear or the like. Further rotation of the central portion 18, as, for example, shown by the arrow 24, enables displaced rotation of the swab head 14, as represented by the arrow 28, which further aids in the cleaning of funnel-shaped cavities such as the auricle of an ear.

Alternatively, as shown in FIG. 2, the swab head 14 may be aligned with the center portion 18 of the elongate member 12. In this instance, the swab 10 may be used to advantage as a conventional swab. Importantly, the swab head 14 is attached to accordion-like folds 36 disposed beneath the cotton swab head 24, and as a result, the expandable accordion-like folds 36 beneath the swab head 14 provide a means for changing the diameter of the swab head 14 as shown in FIG. 3. Any suitable adhesive may be useful in adhering the swab head to the folds 36 with the adhesive, of course, being dependent upon the material of the tube and the swab head. With regard to the swab head 14, any suitable swab material, such as cotton, may be utilized which may be impregnated, treated, covered, or otherwise configured, as is well-known in the art.

Importantly, the presence of the adhesive on the folds 36 allows the folds 22 disposed between the swab head 14 and the central portion 18 to collapse before the folds 36 disposed beneath the swab head 14, when the swab head is forced against an object 40, as shown in FIG. 4. Thus, it can be seen that the folds 22 provide a means for limiting over a selected length of the elongate support member 12, an amount of pressure that can be exerted by the swab head 14 against the object 40 by forcing of the swab head against the object 40 with the elongate support member 12. After collapse of the folds 22 disposed between the head 14 and the center portion 18, shown partially collapsed in FIG. 4, the folds 36 will collapse, thus providing a higher pressure limit that can be exerted by the swab head against the surface 40 and an addition of concomitant diameter increase of the swab head 14, as depicted in FIG. 3.

This feature provides an important function of the articulated swab 10 in accordance with the present invention by reducing a possibility of injury to sensitive portions of a person's body, such as the ear, by over-pressuring of the swab. This over-pressure is avoided by collapsing of the swab and the increased diameter of the swab head 14 which limits the movement of the swab in tight quarters such as a person's ear.

Although there has been hereinabove described a specific arrangement of an applicator swab, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. An applicator swab comprising:
    an elongate support member having a diameter and at least one end;
    a swab head having a different diameter mounted on said at least one end of said elongate support member; and
    means for both adjustably disposing said swab head at an angle to a center portion of said elongate support member and changing the diameter of said swab head.

2. The applicator swab according to claim 1 wherein said elongate support member comprises a tube and said means for adjustably disposing said swab head at an angle to the support member center portion comprises pleated folds in said tube between said swab head and the center portion of said tube.

3. The applicator swab according to claim 1 wherein said means for both adjustably disposing said swab and changing the diameter of said swab head comprises expandable, pleated folds in said tube beneath said swab head.

4. An applicator swab comprising:
    an elongate support having a diameter and at least one end;
    a swab head having a different diameter mounted on said at least one end of said elongate support member; and
    means for changing the diameter of said swab head.

5. The applicator swab according to claim 4 wherein said means for changing the diameter of said swab head comprises expandable pleated folds in said tube beneath said swab head.

6. An applicator swab comprising:
    an elongate support member having a diameter and at least one end;
    a swab head having a different diameter mounted on said at least one end of said elongate support member; and
    means for both limiting, over a selected length of said elongate support member an amount of pressure that can be exerted by the swab head against an object and for changing the diameter of said swab head.

7. The applicator swab according to claim 6 wherein said elongate member comprises a tube and said means for limiting the amount of pressure comprises pleated folds in said tube.

8. The applicator swab according to claim 7 wherein said pleated folds are disposed beneath said swab head and between said swab head and a center portion of said tube, said pleated folds collapsing from an expanded state to a collapsed state to limit the amount of pressure that can be exerted by the swab head.

9. An applicator swab comprising:
    an elongate support member comprising a tube;
    a swab head mounted on at least one end of said elongate support member;
    means for temporarily limiting, over a selected length of said elongate support member, an amount of pressure that can be exerted by the swab head against an object by forcing of said swab head against said object with said elongate support member; said means for limiting pressure comprising pleated folds in said tube, said pleated folds being disposed beneath said swab head and between said swab head and a center portion of said tube, said pleated folds collapsing from an expanded state to a collapsed state to limit the amount of pressure that can be exerted by the swab head; and
    means for causing collapse of the pleated folds between the swab head and the tube center portion before collapse of the pleated folds beneath the swab head as the swab head is forced against the object.

10. The applicator swab according to claim 9 wherein the means for causing collapse of the pleated folds between the swab head and the tube center portion before collapse of the pleated folds beneath the swab head comprises adhesive means for bonding the swab head to the pleated folds therebeneath.

* * * * *